United States Patent [19]
Bennett et al.

[11] Patent Number: 5,968,748
[45] Date of Patent: Oct. 19, 1999

[54] ANTISENSE OLIGONUCLEOTIDE MODULATION OF HUMAN HER-2 EXPRESSION

[75] Inventors: C. Frank Bennett, Carlsbad, Calif.; Allan Lipton, Hershey; Lois M. Witters, York Haven, both of Pa.

[73] Assignees: Isis Pharmaceuticals, Inc., Carlsbad, Calif.; The Penn State Research Foundation, University Park, Pa.

[21] Appl. No.: 09/048,804

[22] Filed: Mar. 26, 1998

[51] Int. Cl.$^6$ .............................. C12Q 1/68; C12N 15/85; C07H 21/04
[52] U.S. Cl. .......................... 435/6; 435/91.1; 435/325; 435/366; 435/375; 536/23.1; 536/24.31; 536/24.5
[58] Field of Search .............................. 435/6, 91.1, 325, 435/366, 375; 536/23.1, 24.31, 24.5

[56] References Cited

U.S. PATENT DOCUMENTS

| | | | |
|---|---|---|---|
| 4,935,341 | 6/1990 | Bargmann et al. | 435/6 |
| 5,034,506 | 7/1991 | Summerton et al. | 528/391 |
| 5,138,045 | 8/1992 | Cook et al. | 536/24.5 |
| 5,218,105 | 6/1993 | Cook et al. | 536/25.31 |
| 5,378,825 | 1/1995 | Cook et al. | 536/25.34 |
| 5,459,255 | 10/1995 | Cook et al. | 536/27.13 |
| 5,539,082 | 7/1996 | Nielsen et al. | 530/300 |

FOREIGN PATENT DOCUMENTS

| | | |
|---|---|---|
| WO 92/20823 | 11/1992 | WIPO . |
| WO 93/09788 | 5/1993 | WIPO . |
| WO 93/24510 | 12/1993 | WIPO . |
| WO 94/17086 | 8/1994 | WIPO . |
| WO 95/17507 | 6/1995 | WIPO . |

OTHER PUBLICATIONS

Berge et al., "Pharmaceutical Salts", *J. Pharma. Sci.*, 1977, 66, 1–19.

Bertram et al., "Reduction of erbB2 gene product in mamma carcinoma cell lines by erbB2 mRNA–specific and tryosine kinase consensus phosphorothioate antisense oligonucleotides", *Biochem. Biophys. Res. Commun.*, 1994, 200(1), 661–667.

Brysch et al., "Inhibition of p185$^{c-erbB-2}$ proto–oncogene expression by antisense oligodeoxynucleotides down–regulates p185–associated tyrosine–kinase activity and strongly inhibits mammary tumor–cell proliferation", *Cancer Gene Ther.*, 1994, 1(2), 99–105.

Casalini et al., "Inhibition of Tumorigenicity in Lung Adenocarcinoma Cells by c–erbB–2 Antisense Expression", *Int. J. Cancer*, 1997, 72, 631–636.

Chang et al., "The tumor suppression activity of E1A in HER–s/neu–overexpression breast cancer", *Oncogene*, 1977, 14, 561–568.

Chiang et al., "Antisense Oligonucleotides Inhibit Intercellular Adhesion Molecule 1 Expression by Two Distinct Mechanisms", *J. Biol. Chem.*, 1991, 266, 18162–18171.

Chonn et al., "Recent advances in liposomal drug–delivery systems", *Curr. Op. Biotech.*, 1995, 6, 698–708.

Cohen et al., "The Relationship between Human Epidermal Growth–like Factor Receptor Expression and Cellular Transformation in NIH3T3 Cells", *J. Biol. Chem.*, 1996, 271(48), 30897–30903.

Colomer et al., "erbB–2 antisense oligonucleotides inhibit the proliferation of breast carcinoma cells with erbB–2 oncogene amplification", *Br. J. Cancer*, 1994, 70, 819–825.

Crooke et al., "Pharmacokinetic Properties of Several Novel Oligonucleotide Analogs in mice", *J. Pharmacol. Exp. Therapeutics*, 1996, 277, 923–937.

De Mesmaeker et al., "Antisense Oligonucleotides", *Acc. Chem. Res.*, 1995, 28, 366–374.

Ebbinghaus et al., "Triplex Formation Inhibits HER–2/neu Transcription in Vitro", *J. Clin. Invest.*, 1993, 92, 2433–2439.

Gebeyehu et al., "Novel bitinylated nucleotide—analogs for labeling and colorimetric detection of DNA", *Nuc. Acids Res.*, 1987, 15, 4513–4534.

Juhl et al., "HER–2/neu is Rate–limiting for Ovarian Cancer Growth", *J. Biol. Chem.*, 1997, 272(47), 29482–29486.

Kabanov et al., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kawasaki et al., "Uniformly Modified 2'–Deoxy–2'–fluoro Phosphorothioate Oligonucleotides as Nuclease–Resistant Antisense Compounds with High Affinity and Specificity for RNA Targets", *J. Med. Chem.*, 1993, 831–841.

Kornberg, *DNA Replication*, W.H. Freeman & Co., San Francisco, 1974, 75–77.

Korutla et al., "Inhibition of ligand–induced activation of epidermal growth factor receptor tyrosine phosphorylation by curcumin", *Carcinogenesis*, 1995, 16(8), 1741–1745.

Kumar et al., "Interferon α induces the expression of retinoblastoma gene product in human Burkitt lymphoma Daudi cells: Role in growth regulation", *Proc. Natl. Acad. Sci. USA*, 1992, 89, 6599–6603.

Lee et al., *Crit. Rev. Therp. Drug Carrier Sys.*, 1991, 8, 91–192.

Letsinger et al., "Cholesterol–conjugated oligonucleotides: Synthesis, properties and activity as inhibitors of replication of human immunodeficiency virus in cell culture", *Proc. Natl. Acad. Sci.*, 1989, 86, 6553–6556.

(List continued on next page.)

*Primary Examiner*—Nancy Degen
*Assistant Examiner*—Andrew Wang
*Attorney, Agent, or Firm*—Woodcock Washburn Kurtz Mackiewicz & Norris LLP

[57] ABSTRACT

Compounds, compositions and methods are provided for inhibiting the expression of human HER-2 (also known as c-neu, ErbB-2 and HER-2/neu). The compositions comprise antisense oligonucleoptides targeted to nucleic acids encoding HER-2. Methods of using these oligonucleotides for inhibition of HER-2 expression and for treatment of diseases such as cancers associated with overexpression of HER-2 are provided. Methods of inhibiting other growth factor receptors using antisense oligonucleotides targeted to nucleic acids encoding HER-2 are also provided.

9 Claims, No Drawings

OTHER PUBLICATIONS

Liu et al., "Inhibition of erbB–2–Positive Breast Cancer Cell Growth by erbB–2 Antisense Oligonucleotides", *Antisense Nucl. Acid Drug Devel.*, 1996, 6, 9–16.

Manoharan et al., "Cholic Acid–Oligonucliotide Conjugates for Antisense Applications", *Bioorganic Med. Chem. Letts.*, 1994, 4, 1053–1060.

Manoharan et al., "Chemical Modifications to Improve Uptake and Bioavailability of Antisense Oligonucleotides", *Ann. NY Acad. Sciences*, 1992, 660, 306–309.

Manoharan et al., "Lipidic Nucleic Acids", *Tetrahedron Letts.*, 1995, 36, 3651–3654.

Manoharan et al., "Oligonucleotide Conjugates: Alteration of the Pharmacokinetic Properties of Antisense Agents", *Nucleosides and Nucleotides*, 1995, 14, 969–973.

Manoharan et al., "Introduction of a Lipophilic Thioether Tether in the Minor Groove of Nucleic Acids for Antisense Applications", *Bioorg. Med. Chem. Letts.*, 1993, 3, 2765–2770.

Martin et al., "Ein neuer Zugang zu 2'–O–Alkylribonucleosiden und Eigenschaften deren Oligonucleotide", *Helvetica Chemica Acta*, 1995, 78, 486–504.

Mishra et al., "Improved leishmanicidal effect of phosphorotioate antisense oligonucleotides by LDL–medicated delivery", *Biochim. Et Biophysica*, 1995, 1264,229–237.

Muranishi, "Absorption, Enhancers", *Crit. Rev. Ther. Drug Carrier Systems*, 1990, 7, 1–33.

Nielsen et al., "Sequence–Selective Recognition of DNA by Strand Displacement with a Thymine–Substituted Polyamide", *Science*, 1991, 254, 1497–1500.

Oberhauser et al., "Effective incorporation of 2'–O–methyl–oligonucleotides into liposomes and enhanced cell association through modification with thiocholesterol", *Nucl. Acids Res.*, 1992, 20, 533–538.

Pegues et al., "Inducible antisense inhibition of erbB–2 expression reduces anchorage independent growth of ovarian carcinoma cells", *Cancer Lett.*, 1997, 117, 73–79.

Porumb et al., "Temporary ex Vivo Inhibition of the Expression of the Human Oncogene HER2 (NEU) by a Triple Helix–forming Oligonucleotide", *Cancer Res.*, 1996, 56, 515–522.

Saison–Behmoaras et al., "Short modified antisense oligonucleotides directed against Ha–ras point mutation induce selective cleavage of the mRNA and inhibit T24 cells proliferation", *EMBO J.*, 1991, 10, 1111–1118.

Sanghvi et al., "Antisense oligodeoxynucleotides: synthesis, biophysical and biological evaluation of oligodeoxynucleotides containing modified pyrimidines", *Nucl. Acids Res.*, 1993, 21, 3197–3203.

Shea et al., "Synthesis, hybridization properties and antiviral activity of lipid–oligodeoxynucletide conjugates", *Nucl. Acids Res.*, 1990, 18, 3777–3783.

Svinarchuk et al., "Inhibition of HIV proliferation in MT–4 cells by antisense oligonucleotide conjugated to lipophilic groups", *Biochimie*, 1993, 79, 49–54.

Tan et al., "Overexpression of the c–erbB–2 Gene Enhanced Intrinsic Metastasis Potential in Human Breast Cancer Cells without Increasing Their Transformation Abilities", *Cancer Res.*, 1997, 57, 1199–1205.

Ueno et al., "Chemosensitization of HER–2/neu–overexpressing human breast cancer cells to paclitaxel (Taxol) by adenovirus type 5 E1A", *Oncogene*, 1997, 15, 953.

Valone et al., "Clinical Trials of Bispecific Antibody MDX–210 in Women with Advanced Breast or Ovarian Cancer that Overexpreses HER–2/neu", *J. Hematotherapy*, 1995, 4, 471–475.

Vaughn et al., "Inhibition of the erbB–2 tyrosine kinase receptor in breast cancer cells by phosphoromonothioate and phosphoroditheoate antisense oligonucleotides", *Nucl. Acids Res.*, 1996, 24(22), 4558–4564.

Wiechen et al., "c–erbB–2 Anti–Sense Phosphorothioate Oligodeoxynucleotides Inhibit Growth and Serum–Induced Cell Spreading of $P185^{c-34bB-2}$–Overexpressing Carcinoma Cells", *Int. J. Cancer*, 1995, 63, 604–608.

Witters et al., "Enhanced anti–proliferative activity of the combination of tamoxifen plus HER–2–neu antibody", *Breast Cancer Res. Treat.*, 1997, 42, 1–5.

Yamamoto et al., "Similarity of protein encoded by the human c–erb–B–2 gene to epidermal growth factor receptor", *Nature*, 1986, 319, 230–234.

Zhang et al., "Sensitization of HER–2/neu–overexpressing non–small cell lung cancer cells to chemotherapeutic drugs by tyrosine kinase inhibitor emodin", *Oncogene*, 1996, 12, 571–576.

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 4473 base pairs
      (B) TYPE: Nucleic Acid
      (C) STRANDEDNESS: Single
      (D) TOPOLOGY: Unknown (iv) ANTI-SENSE: No (xi) SEQUENCE DESCRIPTION: SEQ ID NO: 1:

| | | | | | |
|---|---|---|---|---|---|
| AAGGGGAGGT | AACCCTGGCC | CCTTTGGTCG | GGGCCCCGGG | CAGCCGCGCG | 50 |
| CCCCTTCCCA | CGGGGCCCTT | TACTGCGCCG | CGCGCCCGGC | CCCCACCCCT | 100 |
| CGCAGCACCC | CGCGCCCCGC | GCCCTCCCAG | CCGGGTCCAG | CCGGAGCCAT | 150 |
| GGGGCCGGAG | CCGCAGTGAG | CACCATGGAG | CTGGCGGCCT | TGTGCCGCTG | 200 |
| GGGGCTCCTC | CTCGCCCTCT | TGCCCCCCGG | AGCCGCGAGC | ACCCAAGTGT | 250 |
| GCACCGGCAC | AGACATGAAG | CTGCGGCTCC | CTGCCAGTCC | CGAGACCCAC | 300 |
| CTGGACATGC | TCCGCCACCT | CTACCAGGGC | TGCCAGGTGG | TGCAGGGAAA | 350 |
| CCTGGAACTC | ACCTACCTGC | CCACCAATGC | CAGCCTGTCC | TTCCTGCAGG | 400 |
| ATATCCAGGA | GGTGCAGGGC | TACGTGCTCA | TCGCTCACAA | CCAAGTGAGG | 450 |
| CAGGTCCCAC | TGCAGAGGCT | GCGGATTGTG | CGAGGCACCC | AGCTCTTTGA | 500 |
| GGACAACTAT | GCCCTGGCCG | TGCTAGACAA | TGGAGACCCG | CTGAACAATA | 550 |
| CCACCCCTGT | CACAGGGGCC | TCCCCAGGAG | GCCTGCGGGA | GCTGCAGCTT | 600 |
| CGAAGCCTCA | CAGAGATCTT | GAAAGGAGGG | GTCTTGATCC | AGCGGAACCC | 650 |
| CCAGCTCTGC | TACCAGGACA | CGATTTTGTG | GAAGGACATC | TTCCACAAGA | 700 |
| ACAACCAGCT | GGCTCTCACA | CTGATAGACA | CCAACCGCTC | TCGGGCCTGC | 750 |
| CACCCCTGTT | CTCCGATGTG | TAAGGGCTCC | CGCTGCTGGG | GAGAGAGTTC | 800 |
| TGAGGATTGT | CAGAGCCTGA | CGCGCACTGT | CTGTGCCGGT | GGCTGTGCCC | 850 |
| GCTGCAAGGG | GCCACTGCCC | ACTGACTGCT | GCCATGAGCA | GTGTGCTGCC | 900 |
| GGCTGCACGG | GCCCCAAGCA | CTCTGACTGC | CTGGCCTGCC | TCCACTTCAA | 950 |
| CCACAGTGGC | ATCTGTGAGC | TGCACTGCCC | AGCCCTGGTC | ACCTACAACA | 1000 |
| CAGACACGTT | TGAGTCCATG | CCCAATCCCG | AGGGCCGGTA | TACATTCGGC | 1050 |
| GCCAGCTGTG | TGACTGCCTG | TCCCTACAAC | TACCTTTCTA | CGGACGTGGG | 1100 |
| ATCCTGCACC | CTCGTCTGCC | CCCTGCACAA | CCAAGAGGTG | ACAGCAGAGG | 1150 |
| ATGGAACACA | GCGGTGTGAG | AAGTGCAGCA | AGCCCTGTGC | CCGAGTGTGC | 1200 |
| TATGGTCTGG | GCATGGAGCA | CTTGCGAGAG | GTGAGGGCAG | TTACCAGTGC | 1250 |
| CAATATCCAG | GAGTTTGCTG | GCTGCAAGAA | GATCTTTGGG | AGCCTGGCAT | 1300 |
| TTCTGCCGGA | GAGCTTTGAT | GGGGACCCAG | CCTCCAACAC | TGCCCCGCTC | 1350 |
| CAGCCAGAGC | AGCTCCAAGT | GTTTGAGACT | CTGGAAGAGA | TCACAGGTTA | 1400 |
| CCTATACATC | TCAGCATGGC | CGGACAGCCT | GCCTGACCTC | AGCGTCTTCC | 1450 |
| AGAACCTGCA | AGTAATCCGG | GGACGAATTC | TGCACAATGG | CGCCTACTCG | 1500 |

| | |
|---|---|
| CTGACCCTGC AAGGGCTGGG CATCAGCTGG CTGGGGCTGC GCTCACTGAG | 1550 |
| GGAACTGGGC AGTGGACTGG CCCTCATCCA CCATAACACC CACCTCTGCT | 1600 |
| TCGTGCACAC GGTGCCCTGG GACCAGCTCT TTCGGAACCC GCACCAAGCT | 1650 |
| CTGCTCCACA CTGCCAACCG GCCAGAGGAC GAGTGTGTGG GCGAGGGCCT | 1700 |
| GGCCTGCCAC CAGCTGTGCG CCCGAGGGCA CTGCTGGGGT CCAGGGCCCA | 1750 |
| CCCAGTGTGT CAACTGCAGC CAGTTCCTTC GGGGCCAGGA GTGCGTGGAG | 1800 |
| GAATGCCGAG TACTCAGGG GCTCCCCAGG GAGTATGTGA ATGCCAGGCA | 1850 |
| CTGTTTGCCG TGCCACCCTG AGTGTCAGCC CCAGAATGGC TCAGTGACCT | 1900 |
| GTTTTGGACC GGAGGCTGAC CAGTGTGTGG CCTGTGCCCA CTATAAGGAC | 1950 |
| CCTCCCTTCT GCGTGGCCCG CTGCCCCAGC GGTGTGAAAC CTGACCTCTC | 2000 |
| CTACATGCCC ATCTGGAAGT TTCCAGATGA GGAGGGCGCA TGCCAGCCTT | 2050 |
| GCCCCATCAA CTGCACCCAC TCCTGTGTGG ACCTGGATGA CAAGGGCTGC | 2100 |
| CCCGCCGAGC AGAGAGCCAG CCCTCTGACG TCCATCATCT CTGCGGTGGT | 2150 |
| TGGCATTCTG CTGGTCGTGG TCTTGGGGGT GGTCTTTGGG ATCCTCATCA | 2200 |
| AGCGACGGCA GCAGAAGATC CGGAAGTACA CGATGCGGAG ACTGCTGCAG | 2250 |
| GAAACGGAGC TGGTGGAGCC GCTGACACCT AGCGGAGCGA TGCCCAACCA | 2300 |
| GGCGCAGATG CGGATCCTGA AAGAGACGGA GCTGAGGAAG GTGAAGGTGC | 2350 |
| TTGGATCTGG CGCTTTTGGC ACAGTCTACA AGGGCATCTG GATCCCTGAT | 2400 |
| GGGGAGAATG TGAAAATTCC AGTGGCCATC AAAGTGTTGA GGGAAAACAC | 2450 |
| ATCCCCCAAA GCCAACAAAG AAATCTTAGA CGAAGCATAC GTGATGGCTG | 2500 |
| GTGTGGGCTC CCCATATGTC TCCCGCCTTC TGGGCATCTG CCTGACATCC | 2550 |
| ACGGTGCAGC TGGTGACACA GCTTATGCCC TATGGCTGCC TCTTAGACCA | 2600 |
| TGTCCGGGAA AACCGCGGAC GCCTGGGCTC CCAGGACCTG CTGAACTGGT | 2650 |
| GTATGCAGAT TGCCAAGGGG ATGAGCTACC TGGAGGATGT GCGGCTCGTA | 2700 |
| CACAGGGACT TGGCCGCTCG GAACGTGCTG GTCAAGAGTC CCAACCATGT | 2750 |
| CAAAATTACA GACTTCGGGC TGGCTCGGCT GCTGGACATT GACGAGACAG | 2800 |
| AGTACCATGC AGATGGGGGC AAGGTGCCCA TCAAGTGGAT GGCGCTGGAG | 2850 |
| TCCATTCTCC GCCGGCGGTT CACCCACCAG AGTGATGTGT GGAGTTATGG | 2900 |
| TGTGACTGTG TGGGAGCTGA TGACTTTTGG GGCCAAACCT TACGATGGGA | 2950 |
| TCCCAGCCCG GGAGATCCCT GACCTGCTGG AAAAGGGGGA GCGGCTGCCC | 3000 |
| CAGCCCCCCA TCTGCACCAT TGATGTCTAC ATGATCATGG TCAAATGTTG | 3050 |
| GATGATTGAC TCTGAATGTC GGCCAAGATT CCGGGAGTTG GTGTCTGAAT | 3100 |
| TCTCCCGCAT GGCCAGGGAC CCCCAGCGCT TTGTGGTCAT CCAGAATGAG | 3150 |
| GACTTGGGCC CAGCCAGTCC CTTGGACAGC ACCTTCTACC GCTCACTGCT | 3200 |
| GGAGGACGAT GACATGGGGG ACCTGGTGGA TGCTGAGGAG TATCTGGTAC | 3250 |
| CCCAGCAGGG CTTCTTCTGT CCAGACCCTG CCCCGGGCGC TGGGGCATG | 3300 |
| GTCCACCACA GGCACCGCAG CTCATCTACC AGGAGTGGCG GTGGGACCT | 3350 |
| GACACTAGGG CTGGAGCCCT CTGAAGAGGA GGCCCCCAGG TCTCCACTGG | 3400 |
| CACCCTCCGA AGGGGCTGGC TCCGATGTAT TTGATGGTGA CCTGGGAATG | 3450 |
| GGGGCAGCCA AGGGGCTGCA AAGCCTCCCC ACACATGACC CCAGCCCTCT | 3500 |

```
ACAGCGGTAC AGTGAGGACC CCACAGTACC CCTGCCCTCT GAGACTGATG      3550

GCTACGTTGC CCCCCTGACC TGCAGCCCCC AGCCTGAATA TGTGAACCAG      3600

CCAGATGTTC GGCCCCAGCC CCCTTCGCCC CGAGAGGGCC CTCTGCCTGC      3650

TGCCCGACCT GCTGGTGCCA CTCTGGAAAG GCCCAAGACT CTCTCCCCAG      3700

GGAAGAATGG GGTCGTCAAA GACGTTTTTG CCTTTGGGGG TGCCGTGGAG      3750

AACCCCGAGT ACTTGACACC CCAGGGAGGA GCTGCCCCTC AGCCCCACCC      3800

TCCTCCTGCC TTCAGCCCAG CCTTCGACAA CCTCTATTAC TGGGACCAGG      3850

ACCCACCAGA GCGGGGGGCT CCACCCAGCA CCTTCAAAGG GACACCTACG      3900

GCAGAGAACC CAGAGTACCT GGGTCTGGAC GTGCCAGTGT GAACCAGAAG      3950

GCCAAGTCCG CAGAAGCCCT GATGTGTCCT CAGGGAGCAG GGAAGGCCTG      4000

ACTTCTGCTG GCATCAAGAG GTGGGAGGGC CCTCCGACCA CTTCCAGGGG      4050

AACCTGCCAT GCCAGGAACC TGTCCTAAGG AACCTTCCTT CCTGCTTGAG      4100

TTCCCAGATG GCTGGAAGGG GTCCAGCCTC GTTGGAAGAG GAACAGCACT      4150

GGGGAGTCTT TGTGGATTCT GAGGCCCTGC CCAATGAGAC TCTAGGGTCC      4200

AGTGGATGCC ACAGCCCAGC TTGGCCCTTT CCTTCCAGAT CCTGGGTACT      4250

GAAAGCCTTA GGGAAGCTGG CCTGAGAGGG GAAGCGGCCC TAAGGGAGTG      4300

TCTAAGAACA AAAGCGACCC ATTCAGAGAC TGTCCCTGAA ACCTAGTACT      4350

GCCCCCCATG AGGAAGGAAC AGCAATGGTG TCAGTATCCA GGCTTTGTAC      4400

AGAGTGCTTT TCTGTTTAGT TTTTACTTTT TTTGTTTTGT TTTTTAAAG       4450

ATGAAATAAA GACCCAGGGG GAG                                   4473
```

(2) INFORMATION FOR SEQ ID NO: 2:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 2:

```
GGTCAGGCAG GCTGTCCGGC                                         20
```

(2) INFORMATION FOR SEQ ID NO: 3:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 3:

```
GTCCCCACCG CCACTCCTGG                                         20
```

(2) INFORMATION FOR SEQ ID NO: 4:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 4:

GCATGGCAGG TTCCCCTGGA                                    20

(2) INFORMATION FOR SEQ ID NO: 5:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 5:

GGGCTTCTGC GGACTTGGCC                                    20

(2) INFORMATION FOR SEQ ID NO: 6:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 6:

GTCCCACCCC GCACTCCGTG                                    20

(2) INFORMATION FOR SEQ ID NO: 7:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 7:

GTCCCCACTA CCGCCCCTGG                                    20

(2) INFORMATION FOR SEQ ID NO: 8:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 8:

GTCCCCGACA CCCCTCCTGG                                    20

(2) INFORMATION FOR SEQ ID NO: 9:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 9:

ACTGTCCCCT GGCCACCGCC                                    20

-continued (2) INFORMATION FOR SEQ ID NO: 10:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 10:

GGTGTCCGGC CAGGCAGGCT                    20

ANTISENSE OLIGONUCLEOTIDE MODULATION OF HUMAN HER-2 EXPRESSION

FIELD OF THE INVENTION

The HER-2 proto-oncogene (also known as erbB-2, c-neu and HER-2/neu) is one of the most frequently altered genes in cancer. It encodes a transmembrane receptor (also known as p185) with tyrosine kinase activity and is a member of the epidermal growth factor (EGF) family, and thus is related to the epidermal growth factor receptor (EGFR or HER-1). Other members of EGF family include ErbB-3/HER-3 and ErbB-4/HER-4. The sequence of the human c-erb-B-2 cDNA is 4480 base pairs long and contains a putative transmembrane domain at nucleotides 2135–2199. Yamamoto, et al., *Nature*, 1986, 319, 230. Aberrant HER-2 gene expression is present in a wide variety of cancers and are most common in breast, ovarian and gastric cancers. HER-2 is overexpressed in 25–30% of all human breast and ovarian cancers. Levels of HER-2 overexpression correlate well with clinical stage of breast cancer, prognosis and metastatic potential. Overexpression of HER-2 is associated with lower survival rates, increased relapse rates and increased metastatic potential. Tan, et al., (Cancer Res., 1997, 57, 1199) have shown that overexpression of the HER-2 gene increases the metastatic potential of breast cancer cells without increasing their transformation ability.

Aberrant expression of HER-2 includes both increased expression of normal HER-2 and expression of mutant HER-2. Activation of the HER-2 proto-oncogene can occur by any of three mechanisms—point mutation, gene amplification and overexpression. Gene amplification is the most common mechanism. Unlike the other EGF family members for which ligand activation is necessary for promoting transformation, overexpression of HER-2 alone is sufficient for transformation. Cohen, et al., *J. Biol. Chem.*, 1996, 271, 30897.

Several therapeutic approaches have been used to reduce levels of th HER-2 gene product. The adenovirus type 5 gene product E1A, has been studied as a potential therapeutic using a breast cancer model in nude mice. This gene product can repress HER-2/neu overexpression by repressing HER-2/neu promoter activity, and suppress the tumorigenic potential of HER-2/neu-overexpressing ovarian cancer cells. In mice bearing HER-2/neu-overexpressing breast cancer xenografts, E1A delivered either by adenovirus or liposome significantly inhibited tumor growth and prolonged mouse survival compared with the controls. Chang, et al., *Oncogene*, 1997, 14, 561.

Clinical trials have been conducted to evaluate a bispecific antibody which targets the extracellular domains of both the HER-2/neu protein product and Fc gamma RIII (CD16), the Fc gamma receptor expressed by human natural killer cells, neutrophils, and differentiated mononuclear phagocytes. Weiner, et al., *J. of Hematotherapy*, 1995, 4, 471.

Overexpression of HER-2 has also been found to be associated with increased resistance to chemotherapy. Thus, patients with elevated levels of HER-2 respond poorly to many drugs. It is believed that decreasing the levels of HER-2 will allow chemotherapeutic drugs to be more effective. Methods used to inhibit HER-2 expression have been combined with commonly used chemotherapeutic agents. Ueno, et al. (*Oncogone*, 1997, 15, 953) combined the adenovirus type 5 gene product, E1A, with taxol and showed a synergistic effect in human breast cancer cells. Zhang, et al. (*Oncogene*, 1996, 12, 571) demonstrated that emodin, a tyrosine-specific inhibitor, sensitized non-small cell lung cancer (NSCLC) cells to a variety of chemotherapeutic drugs, including cisplatin, doxorubicin and etoposide. A HER-2 antibody was found to increase the efficacy of tamoxifen in human breast cancer cells. Witters, et al., *Breast Cancer Res. and Treatment*, 1997, 42, 1).

Oligonucleotides have also been used to study the function of HER-2. A triplex-forming oligonucleotide targeted to the HER-2 promoter, 42 to 69 nucleotides upstream of the mRNA transcription start site, was found to inhibit HER-2 expression in vitro. Ebbinghaus, et al., *J. Clin. Invest.*, 1993, 92, 2433). Porumb, et al. (Cancer Res., 1996, 56, 515) also used a triplex-forming oligonucleotide targeted to the same HER-2 promoter region. Decreases in HER-2 mRNA and protein levels were seen in cultured cells. Juhl, et al. (*J. Biol. Chem.*, 1997, 272, 29482) used anti-HER-2 ribozymes targeted to a central region of the HER-2 RNA just downstream of the transmembrane region of the protein to demonstrate a reduction in HER-2 mRNA, protein levels in human ovarian cancer cells. A reduction in tumor growth in nude mice was also seen.

An antisense approach has been used as a potential therapeutic for HER-2 overexpressing cancers. Pegues, et al. (*Cancer Lett.*, 1997, 117, 73) cloned a 1.5 kb fragment of HER-2 in an antisense orientation into an expression vector; transfecting of this construct into ovarian cancer cells resulted in a reduction of anchorage-independent growth. Casalini, et al. (*Int. J. Cancer*, 1997, 72, 631) used several human HER-2 antisense vector constructs, containing HER-2 fragments from 151 bp to 415 bp in length, to demonstrate reduction in HER-2 protein levels and anchorage-independent growth in lung adenocarcinoma cells. Colomer, et al. (*Br. J. Cancer*, 1994, 70, 819) showed that phosphodiester antisense oligonucleotides targeted at or immediately downstream of, the translation initiation codon inhibited proliferation of human breast cancer cells by up to 60%. Wiechen, et al. (*Int. J. Cancer*, 1995, 63, 604) demonstrated that an 18-nucleotide phosphorothioate oligonucleotide targeted to the coding region, 33 nucleotides downstream of the translation initiation codon, of HER-2 reduced anchorage-independent growth of ovarian cancer cells. Bertram, et al. (*Biochem. Biophys. Res. Commun.*, 1994, 200, 661) used antisense phosphorothioate oligonucleotides targeted to the translation initiation region and a sequence at the 3' part of the translated region of the mRNA which has high homology to a tyrosine kinase consensus sequence, and demonstrated a 75% reduction in HER-2 protein levels in human breast cancer cells. Liu, et al., (*Antisense and Nucleic Acid Drug Develop.*, 1996, 6, 9) used antisense phosphorothioate oligonucleotides targeted to the 5' cap site and coding region. Their most effective oligonucleotide, targeted to the 5' cap site, reduced HER-2 protein expression by 90%. Cell proliferation was also reduced by a comparable amount. Vaughn, et al. (*Nuc. Acids. Res.*, 1996, 24, 4558) used phosphorothioate, phosphorodithioate and chimeric antisense oligonucleotides targeted at or adjacent to (either side) the translation initiation region of HER-2. An alternating dithioate/diester oligonucleotide targeted to the translation initiation region worked slightly better than an all phosphorothioate oligonucleotide. Brysch, et al. (*Cancer Gene Ther.*, 1994, 1, 99) used chemically modified antisense oligonucleotides targeted to the translation initiation codon of HER-2 to reduce protein levels and cause growth arrest of human breast cancer cell line.

WO 94/17086 discloses oligonucleotides targeted to regions of DNA that are believed to have a non-B form, due to palindromic regions. Among these is a triplex forming oligonucleotide targeted to the promoter region of ErbB-2. WO 93/09788 discloses additional triplex-forming oligonucleotides targeted to the promoter region of erb B2/neu.

WO 95/17507 discloses antisense oligonucleotides hybridizing with mRNA or DNA encoding c-erbB-2, having a DNA-type or RNA-type structure. However, no data is present for any particular oligonucleotide sequence.

U.S. Pat. No. 4,935,341 discloses oligonucleotide probes capable of hybridizing specifically with the region of mutational activation in the transmembrane domain of a neu gene of mammalian origin. Also disclosed are oligonucleotide probes capable of hybridizing to a sequence present in the transmembrane domain of a neu oncogene of mammalian origin which is not present in the corresponding protooncogene. However, no human sequences are disclosed.

There remains a long-felt need for improved compositions and methods for inhibiting HER-2 gene expression.

SUMMARY OF THE INVENTION

The present invention provides antisense oligonucleotides which are targeted to nucleic acids encoding human HER-2 and are capable of inhibiting HER-2 expression. The oligonucleotides of the invention are believed to be useful both diagnostically and therapeutically, and are believed to be particularly useful in the methods of the present invention. Pharmaceutical compositions comprising the antisense oligonucleotides of the invention are also provided.

The present invention also comprises methods of inhibiting the expression of human HER-2, using the compositions of the invention. These methods are believed to be useful both therapeutically and diagnostically as a consequence of the association between HER-2 expression and hyperproliferation. These methods are also useful as tools, for example, for detecting and determining the role of HER-2 expression in various cell functions and physiological processes and conditions and for diagnosing conditions associated with HER-2 expression.

The present invention also comprises methods of reducing hyperproliferation of cells using oligonucleotides and compositions of the invention. These methods are believed to be useful, for example, in diagnosing HER-2-associated cell hyperproliferation. Methods of treating abnormal proliferative conditions are also provided. These methods employ the oligonucleotides of the invention.

Methods of decreasing growth factor receptor expression using antisense oligonucleotides targeted to HER-2 are also provided. These methods are believed to be useful therapeutically, diagnostically and as research tools.

DETAILED DESCRIPTION OF THE INVENTION

The present invention employs antisense compounds, particularly oligonucleotides, for use in inhibiting the function of nucleic acid molecules encoding HER-2, ultimately modulating the amount of HER-2 produced. This is accomplished by providing oligonucleotides which specifically hybridize with nucleic acids, preferably mRNA, encoding HER-2.

This relation hip between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding HER-2; in other words, a HER-2 gene or RNA expressed from a HER-2 gene. HER-2 mRNA is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5═ cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding HER-2, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions may also be preferred targets.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted. For example, an oligonucleotide may be specifically hybridizable to a target nucleic acid molecule if the oligonucleotide sequence is preferably greater than 70%, more preferably greater than 80% and most preferably greater than 90% complementary to the nucleotide sequence of the target nucleic acid molecule.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA.

The overall effect of interference with mRNA function is modulation of HER-2 expression. In the context of this invention "modulation" means either inhibition or stimulation; i.e., either a decrease or increase in expression. Inhibition of HER-2 gene expression is presently the preferred form of modulation. This modulation can be measured in ways which are routine in the art, for example, by Northern blot assay of mRNA expression as taught in the examples of the instant application or by Western blot or ELISA assay of protein expression, or by an immunoprecipitation assay of protein expression, as taught in the examples of the instant application. Effects on cell proliferation or tumor cell growth can also be measured, as taught in the examples of the instant application.

The oligonucleotides of this invention can be used in diagnostics, therapeutics, prophylaxis, and as research reagents and in kits. Since the oligonucleotides of this invention hybridize to nucleic acids encoding HER-2, sandwich, colorimetric and other assays can easily be constructed to exploit this fact. Furthermore, since the oligonucleotides of this invention hybridize specifically to nucleic acids encoding particular isozymes of HER-2, such assays can be devised for screening of cells and tissues for particular HER-2 isozymes. Such assays can be utilized for diagnosis of diseases associated with various HER-2 forms. Provision of means for detecting hybridization of oligonucleotide with a HER-2 gene or mRNA can routinely be accomplished. Such provision may include enzyme conjugation, radiolabelling or any other suitable detection systems. Kits for detecting the presence or absence of HER-2 may also be prepared.

The present invention is also suitable for diagnosing abnormal proliferative states in tissue or other samples from patients suspected of having a hyperproliferative disease such as cancer or psoriasis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal. Similarly, the present invention can be used to distinguish HER-2-associated tumors, particularly tumors associated with HER-2α, from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid, or both. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates (usually abbreviated in the art as P=S) and those with $CH_2$—NH—O—$CH_2$, $CH_2$—N($CH_3$)—O—$CH_2$ [known as a methylene (methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester (usually abbreviated in the art as P=O) backbone is re resented as O—P—O—$CH_2$). Also preferred are oligonucleotide having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker, et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone. Nielsen, et al., *Science*, 1991, 254, 1497 and U.S. Pat. No. 5,539,082. Other preferred modified oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_n NH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-O-methoxyethyl, which can be written as 2'—O—$CH_2COCH_3$, and is also known in the art as 2'-O-(2-methoxyethyl) or 2'-methoxyethoxy. Martin, et al., *Helv. Chim. Acta*, 1995, 78, 486. Other preferred modifications include 2'-methoxy (2'—O—$CH_3$), 2'-propoxy (2'—$OCH_2CH_2CH_3$) and 2'-fluoro (2'-F). Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonuclotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine and 5-methylcytosine, as well as synthetic nucleobases, e.g., 5-bromouracil, 5-hydroxymethyluracil, 8-azaguanine, 7-deazaguanine, $N^6$(6-aminohexyl)adenine and 2,6-diaminopurine. Kornberg, DNA Replication, 1974, W. H. Freeman & Co., San Francisco, 1974, pp 75–77; and Gebeyehu, et al., *Nucleic Acids Res.*, 1987, 15, 4513. 5-methylcytosine (5-me-C) is presently a preferred nucleobase, particularly in combination with 2'-O-methoxyethyl modifications.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine nucleobase may also be utilized to link a lipophilic moiety to an oligonucleotide of the invention. Gebeyehu, et al., *Nucleic Acids Res.*, 1987, 15, 4513. Such lipophilic moieties include but are not limited to a cholesteryl moiety (Letsinger, Let al., *Proc. Natl. Acad. Sci. USA*, 1989, 86, 6553), cholic acid (Manoharan, et al., Bioorg. Med. Chem. et., 1994, 4, 1053), a thioether, e.g., hexyl-S-tritylthiol (Manoharan, et al., *Ann. N.Y. Acad. Sci.*, 1992, 660, 306; and Manoharan, et al., *Bioorg. Med. Chem. Let.*, 1993, 3, 2765), a thiocholesterol (Oberhauser, et al., *Nucl. Acids Res.*, 1992, 20, 533), an aliphatic chain, e.g., dodecandiol or undecyl residues (Saison-Behmoaras, et al., *EMBO J.*, 1991, 10, 111; Kabanov, et al., *FEBS Lett.*, 1990, 259, 327; and Svinarchuk, et al., *Biochimie*, 1993, 75 49), a phospholipid, e.g., di-hexadecyl-rac-glycerol or triethylammonium 1,2-di-O-hexadecyl-rac-glycero-3-H-phosphonate (Manoharan, et al., *Tetrahedron Lett.*, 1995, 36, 3651); and Shea, et al., *Nucl. Acids Res.*, 1990, 18, 3777), a polyamine or a polyethylene glycol chain (Manoharan, et al., *Nucleosides & Nucleotides*, 1995, 14, 969), or adamantane acetic acid (Manoharan, et al., *Tetrahedron Lett.*, 1995, 36, 3651), a palmityl moiety (Mishra, et al., *Biochim. Biophys. Acta*, 1995, 1264, 229), or an octadecylamin or hexylamino-carbonyl-oxycholesterol moiety (Crooke, et l., *J. Pharmacol. Exp. Ther.*, 1996, 277, 923). Oligonucleotides comprising lipophilic moieties, and methods for preparing such oligonucleotides, as disclosed in U.S. Pat. Nos. 5,138,045, 5,218,105 and 5,459,255, the contents of which are incorporated herein by reference in their entirety.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted). Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'—O—H$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH$_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred. Through use of such modifications, active oligonucleotides have been identified which are shorter than conventional "first generation" oligonucleotides active against HER-2. Oligonucleotides in accordance with this invention are preferably from 5 to 50, more preferably from 8 to 45, more preferably from 10 to 40, and most preferably from 12 to 25 nucleotides in length. In the context of this invention it is understood that this encompasses non-naturally occurring oligomers as hereinbefore described, having from 5 to 50, 8 to 45, 10 to 40, or 12 to 25 monomers.

The oligonucleotides used in accordance with this invention may be coveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides. Martin, *Helv. Chim. Acta*, 1995, 78, 486. It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids.

"Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge, et al., "Pharmaceutical Salts," *J. of Pharma Sci.*, 1977, 66, 1).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid phosphoric acid, nitric acid and the like; (c) salts formed with organic acids such as, for example, acetic acid oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioetyl) phosphate] derivatives according to the methods disclosed in WO 93/24510 to Gosselin, et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, reservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants. Lee, et al., *Critical Reviews in Therapeutic Drug Carrier Systems*, 1991, 8:91–192 and Muranishi, *Critical Reviews in Therapeutic Drug Carrier Systems*, 1990, 7, 1. One or more penetration enhancers from one or more of these broad categories may be included. Compositions comprising oligonucleotides and penetration enhancers are disclosed in co-pending U.S. patent application Ser. No. 08/886,829 to Teng, et al., filed Jul. 1, 1997, which is incorporated herein by reference in its entirety.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn, et al., *Current Op. Biotech.*, 6, 1995, 698). Liposomal antisense compositions are prepared according to the disclosure of co-pending U.S. patent application Ser. No. 08/961,469 to Hardee, et al., filed Oct. 31, 1997, which is incorporated herein by reference in its entirety.

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, continuous infusion, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration. Modes of administering oligonucleotides are disclosed in co-pending U.S. patent application Ser. No. 08/961,469 to Hardee, et al., filed Oct. 31, 1997, which is incorporated herein by reference in its entirety.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are no intended to limit the same.

EXAMPLES

Example 1: Synthesis of Oligonucleotides

Unmodified oligodeoxynucleotides are synthesized on an automated DNA synthesizer (Applied Biosystems model 380B) using standard phoshoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one-1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham, Mass.) and th standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki, et al., *J. Med. Chem.*, 1993, 36, 831, incorporated herein by reference in its entirety. Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group.

Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl- (DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a known procedure in which 2,2'-anhydro-1-β-D-arabinofuranosyluracil was treated with 70% hydrogen fluoride-pyridine. Standard procedures were used to obtain the 5'-DMT and 5'-DMT-3'phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3'phosphoramidites.

2'-(2-methoxyethyl)-modified amidites are synthesized according to Martin, *Helv. Chim. Acta*, 1995, 78, 486, incorporated herein by reference in its entirety. For ease of synthesis, the last nucleotide was a deoxynucleotide. 2'—O—$CH_2CH_2OCH_3$-cytosines may be 5-methyl cytosines.

Synthesis of 5-Methyl cytosine monomers: 2,2'-Anhydro [1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyetyl-5-methyluridine (160 g, 0.506 M) was co-evaporated with pyridine (250 mL) and the dried residue dissolved in pyridin (1.3 L). A first aliquot of di-methoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (2.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxythyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methyl-cytidine:

2'-O-Methoxyethyl-5'-O-dimethoxytrityl-5-methyl-cytidine (85 g, 0.134 M) was dissolved in DMF (800 mL) and benzoic anhydride (37.2 g, 0.165 M) was added with stirring. After stirring for hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite:

$N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 9) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi, et al., *Nucl. Acids Res.*, 1993, 21, 3197, which is incorporated herein by reference in its entirety) using commercially available phosphoramidites (Glen Research, Sterling Va. or ChemGenes, Needham Mass.).

Oligonucleotides having methylene(methylimino) (MMI) backbones are synthesized according to U.S. Pat. No. 5,378,825, which is coassigned to the assignee of the present invention and is incorporated herein by reference in its entirety. For ease of synthesis, various nucleoside dimers containing MMI linkages were synthesized and incorporated into oligonucleotides. Other nitrogen-containing backbone are synthesized according to WO 92/20823 which is also coassigned to the assignee of the present invention and incorporated herein by reference in its entirety.

Oligonucleotides having amide backbones are synthesized according to De Mesmaeker, et al., *Acc. Chem. Res.*, 1995, 28, 366). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to Nielsen, et al., *Science*, 1991, 254, 1497, which is incorporated herein by reference in its entirety.

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang, et al., *J. Biol. Chem.*, 1991, 266, 18162. Results obtained with HPLC-purified material were similar to those obtained with non-HPLC purified material.

Example 2: Cell Culture

Human SKOV3 ovarian carcinoma cells were obtained from the American Type Culture Collection. They were grown in McCoy's 5A medium containing $NaHCO_3$, 10% fetal bovine serum and routinely passaged.

Example 3: Treatment of Cells with Oligonucleotide

SKOV3 cells were grown in T-75 flasks until 65–75% confluent. The cells were washed once with serum-free OPTI-MEM® medium (Life Technologies, Inc., Grand Island, N.Y.) and 5 ml of the serum-free OPTI-MEM® containing 15 μg/ml of LIPOFECTIN® reagent (a 1:1 liposome formulation of the cationic lipid DOTMA and DOPE, Life Technologies, Inc.) was added. At that time, 300 nM of oligonucleotide was added and swirled vigorously. After a 4 hour incubation at 37° C., the solution was removed and fresh maintenance medium containing 10% fetal bovine serum was added. The cells were again incubated overnight at 37° C., after which the cells were assayed for HER-2 mRNA expression.

Example 4: Measurement of HER-2 mRNA by Northern Blot Analysis

Total mRNA was extracted from the SKOV3 cells by washing cells twice with PBS and adding 1–2 ml of RNA-ZOL B® (Tel-Test, Inc., Friendswood, Tex.). An incubation at 4° C. for 5–30 minutes was done and the cells were scraped into an Eppendorf tube. This solution was frozen at -80° C. for 20 minutes, thawed and chloroform (200 μl/ml) was added. The solution was centrifuged at 12,000×g for 15 minutes at 4° C. and the aqueous layer was transferred to a clean Eppendorf tube. An equal volume of isopropanol was added and incubated at room temperature for 15 minutes. Another centrifugation at 12,000×g for 15 minutes at 4° C. was done. The pellet was washed with 500 μl of 75% ethanol and centrifuged at 7500×g for 5 minutes at 4° C. As much of the supernatant as possible was removed and the pellet was resuspended in 30 μl of double distilled water. Ten μg of mRNA was resolved on a 1.0% agarose gel containing 3.0% formaldehyde and transferred to a nylon membrane. The membrane was hybridized with an asymmetric PCR-generated human HER-2 probe radiolabeled with [α-$^{32}$P]-dCTP (Dupont NEN Research Products, Boston, Mass.).

The HER-2 probe was generated with the pTRI-erbB2-Human transcription template (Ambion, Austin, Tex.) using the GeneAMP PCR Reagent Kit (Perkin Elmer, Foster City, Calif.) and a T7 primer. The membrane was exposed to autoradiography film at −80° C. and the mRNA bands quantitated using a densitometer (Molecular Dynamics). Blots were stripped of radioactivity by boiling and then reprobed with a $^{32}$P-labeled control probe which hybridized to G3PDH (Clontech Laboratories, Inc., Palo Alto, Calif.).

Example 5: Metabolic Labeling and Immunoprecipitation of HER-2

SKOV3 cells were treated with the indicated oligonucleotides in serum-free, methionine-free OPTI-MEM® medium for 2.5 hours. The medium was then replaced with methionine-free OPTI-MEM® containing $^{35}$S-methionine (100 μCi/ml) and 2% dialyzed fetal bovine serum for 10 hours. Cell extracts were prepared as described by Kumar, et al., *Proc. Natl. Acad. Sci. USA*, 1992, 89, 6599. Aliquots

TABLE 1

Nucleotide Sequences of Human HER-2 Oligonucleotides

| ISIS NO. | OLIGONUCLEOTIDE SEQUENCE[1] | SEQ ID: | POSITION ON TARGET[2] | TARGET REGION | CHEMISTRY |
|---|---|---|---|---|---|
| 9002 | GGTCAGGCAGGCTGTCCGGC | 2 | 1419–1438 | Coding | P=S; 2'-deoxy |
| 9003 | GTCCCCACCGCCACTCCTGG | 3 | 3329–3348 | Coding | P=S; 2'-deoxy |
| 9005 | GCATGGCAGGTTCCCCTGGA | 4 | 4043–4062 | 3'-UTR | P=S; 2'-deoxy |
| 12882 | GTCCCCACCGCCACTCCTGG | 3 | 3329–3348 | Coding | P=S; 2'-deoxy, all C's are 5-me-C |
| 12883 | GTCCCCACCGCCACTCCTGG | 3 | 3329–3348 | Coding | P=S; bold = 2'-O-propyl |
| 12884 | GTCCCCACCGCCACTCCTGG | 3 | 3329–3348 | Coding | P=S; bold = 2'-fluoro; all 2'-fluoro C are 5-me-C |
| 12137 | GTCCCCACTACCGCCCCTGG | 7 | scramble of 9003 | | P=S; 2'-deoxy |

[1]Oligonucleotide sequences are written 5' -to- 3'; all linkages are phosphorothioate linkages.
[2]Numbers given are nucleotide numbers on target sequence (Genbank Accession No. X03363, locus name "HSERB2R", provided herein as SEQ ID NO: 1) to which the oligonucleotide is complementary.

The oligonucleotides shown in Table 1 were tested for their ability to reduce HER-2 mRNA levels in the SKOV3 human ovarian carcinoma cell line. mRNA levels were determined by Northern blot analysis as described in Example 4. The results are shown in Table 2.

TABLE 2

Reduction of Human HER-2 mRNA Levels by Antisense Oligonucleotides Targeted to HER-2

| ISIS NO. | SEQ ID NO: | TARGET REGION | CHEMISTRY | % INHIB. |
|---|---|---|---|---|
| 9002 | 2 | Coding | P=S; 2'-deoxy | 72% |
| 9003 | 3 | Coding | P=S; 2'-deoxy | 54% |
| 9005 | 4 | 3'-UTR | P=S; 2'-deoxy | 79% |
| 12882 | 3 | Coding | P=S; 2'-deoxy, all C's are 5-me-C | 85% |
| 12883 | 3 | Coding | P=S; bold = 2'-O-propyl | 91% |
| 12884 | 3 | Coding | P=S; bold = 2'-fluoro; all 2'-fluoro C are 5-me-C | 96% |
| 12137 (control) | 7 | scramble of 9003 | P=S 2' deoxy | 0 |
| None | | | | 0 |

As shown in Table 2, all three phosphorothioate-2'-deoxy oligonucleotides inhibited HER-2 mRNA levels by over 50% in this assay. These compounds are preferred. The second generation compounds (modified chemistry) were even more active than the parent compound, and gave near-total reduction of HER-2 mRNA levels. These compounds are highly preferred.

containing equal amounts of trichloroacetic acid-precipitable counts per minute were subjected to immunoprecipitation with c-erbB-2/HER-2/neu Ab-2 (clone 9G6, NeoMarker (Fremont, Calif.)) monoclonal antibody/rabbit anti-mouse IgG/protein A-Sepharose conjugate. Kumar, et al., *Proc. Natl. Acad. Sci. USA*, 1992, 89, 6599 and Korutla, et al., *Carcinogenesis*, 1995, 16, 1741. Lysates containing equal amounts of protein were also resolved on a 10% SDS-polyacrylamide gel and stained with Coomassie blue. Densitometer scans of the autoradiographed gels allowed calculation of percent reduction of HER-2 protein levels in cells treated with antisense oligonucleotides, compared to cells treated with crambled controls. Results are shown in Table 3:

TABLE 3

Reduction of Human HER-2 Protein Levels by Antisense Oligonucleotides Targeted to HER-2

| ISIS NO. | SEQ ID NO:: | % INHIBITION |
|---|---|---|
| 9002 | 2 | 82% |
| 9003 | 3 | 66% |
| 9005 | 4 | 62% |
| 12882 | 3 | 70% |
| 12883 | 3 | 64% |
| 12884 | 3 | 72% |
| 12137 | 7 | 0 |

All the antisense olgonucleotides inhibited HER-2 protein levels by approximately 60–75%.

Example 6: Analysis of Antisense Effects on the Growth of SKOV3 Cells

SKOV3 cells were treated with oligonucleotides (antisense or scrambled) as described in Example 3 or left untreated as controls. Cells were treated on days 0 and 1, then allowed to grow in maintenance medium with 10% fetal bovine serum and counted on a Coulter counter on day 2.

Effect of antisense oligonucleotides on cell proliferation was calculated as percent of untreated control and expressed as percent inhibition of proliferation compared to control. Results are shown in Table 4.

TABLE 4

Reduction of SKOV3 cell proliferation by Antisense Oligonucleotides Targeted to HER-2

| ISIS NO. | SEQ ID NO: | % INHIBITION |
|---|---|---|
| 9002 | 2 | 38% |
| 9003 | 3 | 26% |
| 9005 | 4 | 32% |
| 12882 | 3 | 45% |
| 12883 | 3 | 22% |
| 12884 | 3 | 61% |

TABLE 4-continued

Reduction of SKOV3 cell proliferation by Antisense Oligonucleotides Targeted to HER-2

| ISIS NO. | SEQ ID NO: | % INHIBITION |
|---|---|---|
| 12137 (control) | 7 | 0 |
| None | — | 0 |

Example 7: Additional Antisense Oligonucleotides Targeted to Human HER-2

Additional antisense oligonucleotides targeted to human HER-2 were synthesized. These are shown in Table 5:

TABLE 5

Nucleotide Sequences of Additional Human HER-2 Oligonucleotides

| ISIS NO | OLIGONUCLEOTIDE SEQUENCE[1] | SEQ ID: | POSITION ON TARGET[2] | TARGET REGION | CHEMISTRY |
|---|---|---|---|---|---|
| 9004 | GsGsGsCsTsTsCsTsGsCsGsGsAsCsTsTsGsGsCsC | 5 | 3950–3969 | 3'-UTR | P=S; 2'-deoxy |
| 12136 | GsTsCsCsCsAsCsCsCsGsCsGsAsCsTsCsCsGsTsG | 6 | scramble of 9003 | | P=S; 2'-deoxy |
| 12137 | GsTsCsCsCsCsAsCsTSAsCsCsGsCsCsCsCsTsGsG | 7 | scramble of 9003 | | P=S; 2'-deoxy |
| 12881 | GsGsGsCsTsTsCsTsGsCsGsGsAsCsTsTsGsGsCsC | 5 | 3950–3969 | 3'-UTR | P=S; 2'-deoxy/ 2'-F; all 2'-F C's are 5-meC |
| 12886 | GsGsTsCsAsGsGsCsAsGsGsCsTsGsTsCsCsGsGsC | 2 | 1419–1438 | Coding | P=S; 2'-deoxy/ 2'-F; all 2'-F C's are 5-meC |
| 15588 | GoToCoCoCoCoAsCsCsGsCsCsAsCsToCoCoToGoG | 3 | 3329–3348 | Coding | P=S/P=O; 2'-deoxy/2'-MOE; all C's = 5-meC |
| 15589 | GsTsCsCsCsAsCsCsGsCsCsAsCsTsCsCsTsGsG | 3 | 3329–3348 | Coding | P=S; 2'-deoxy/2'-MOE; all C's = 5-meC |
| 15590 | GoToCoCoCoCoAoCoCoGsCsCsAsCsTsCsCsTsGsG | 3 | 3329–3348 | Coding | P=S/P=O; 2'-deoxy/2'-MOE; all C's = 5-meC |
| 15591 | GsTsCsCsCsGsAsCsAsCsCsCsTsCsCsTsGsG | 8 | scramble of 9003 | | P=S; 2'-deoxy/2'-MOE; all C's = 5-meC |
| 15592 | GsCsAsTsGsGsCsAsGsGsToToCoCoCoCoToGoGoA | 4 | 4043–4062 | 3'-UTR | P=S/P=O; 2'-deoxy/2'-MOE |
| 17378 | GsCsAsTsGsGsCsAsGsGoToToCoCoCoCoToGoGoA | 4 | 4043–4062 | 3'-UTR | P=S/P=O; 2'-deoxy/2'-MOE |
| 17391 | GsCsAsTsGsGsCsAsGsGsTsTsCsCsCsCsTsGsGsA | 4 | 4043–4062 | 3'-UTR | P=S; 2'-deoxy/2'-MOE |
| 17397 | AsCsTsGsTsCsCsCsTsGsGsCsCsAsCsCsGsCsC | 9 | scramble of 9003 | | P=S; 2'-deoxy |
| 17398 | GsGsTsGsTsCsCsGsGsCsCsAsGsGsCsAsGsGsCsT | 10 | scramble of 9002 | | P=S; 2'-deoxy |
| 17426 | AoCoToGoTsCsCsCsTsGsGsCsCsAoCoCoGoCoC | 9 | scramble of 9003 | | P=S/P=O 2'-deoxy/2'-MOE |
| 17427 | GoGoToGoTsCsCsGsGsCsCsAsGsGsCoAoGoGoCoT | 10 | scramble of 9002 | | P=S/P=O; 2'-deoxy/2'-MOE |
| 17428 | GoGoToCoAsGsGsCsAsGsGsCsTsGsTsCoCoGoGoC | 2 | 1419–1438 | Coding | P=S/P=O; 2'-deoxy/2'-MOE |

TABLE 5-continued

Nucleotide Sequences of Additional Human HER-2 Oligonucleotides

| ISIS NO | OLIGONUCLEOTIDE SEQUENCE[1] | SEQ ID: | POSITION ON TARGET TARGET[2] | TARGET REGION | CHEMISTRY |
|---|---|---|---|---|---|
| 17612 | GoToCoCoCoCsAsCsCsGsCsCsAsCsToCoCoToGoG | 3 | 3329–3348 | Coding | P=S/P=O; 2'-deoxy/2'-MOE |

[1]Oligonucleotide sequences are written 5' -to- 3';
[2]Numbers given are nucleotide numbers on target sequence (Genbank Accession No. X03363, locus name "HSERB2R", provided herein as SEQ ID NO: 1) to which the oligonucleotide is complementary.
[3]Emboldened residues, 2'-methoxyethoxy- residues (others are 2'-deoxy- if not otherwise indicated); all 2'-methoxyethoxy-cytidines are 5-methyl-cytidines.
Underlined residues are indicated chemistry; 2'-F = 2'-fluoro. In backbones, "s" indicates phosphorothioate linkage; "o" indicates phosphodiester linkage.

Compounds shown in Table 5 were tested for the ability to decrease HER-2 mRNA levels in SKOV3 cells as described in Example 4. The results are shown in Table 6.

TABLE 6

Reduction of Human HER-2 mRNA Levels by Antisense Oligonucleotides Targeted to HER-2

| ISIS NO. | SEQ ID: | POSITION ON TARGET[2] | TARGET REGION | % INHIB. (AVERAGED; n = number of expts) | |
|---|---|---|---|---|---|
| 9004 | 5 | 3950–3969 | 3'-UTR | 47 | n = 2 |
| 12136 | 6 | scramble of 9003 | | 0 | n = 2 |
| 12137 | 7 | scramble of 9003 | | 10 | n = 5 |
| 12881 | 5 | 3950–3969 | 9004 | 59 | n = 2 |
| 12886 | 2 | 1419–1438 | 9002 | 43 | n = 2 |
| 17378 | 4 | 4043–4062 | 9005 | 47 | n = 1 |
| 17391 | 4 | 4043–4062 | 9005 | 63 | n = 2 |
| 17397 | 9 | scramble of 9003 | | 0 | n = 1 |
| 17398 | 10 | scramble of 9002 | | 0 | n = 1 |
| 17426 | 9 | scramble of 9003 | | 3 | n = 2 |
| 17427 | 10 | scramble of 9002 | | 0 | n = 2 |
| 17428 | 2 | 1419–1438 | 9002 | 46 | n = 1 |
| 17612 | 3 | 3329–3348 | 9003 | 9 | n = 1 |

Oligonucleotide 9004 (SEQ ID NO:5) inhibited HER-2 mRNA by nearly 50% in this assay and is therefore preferred. Modified oligonucletides 12881, 12886, 17378, 17391 and 17428 inhibited HER-2 mRNA levels by at least 40% in this assay and are therefore preferred.

Example 8: Ability of Antisense Oligonucleotides Targeted to HER-2 to Inhibit Epidermal Growth Factor Receptor (EGFR) Expression Oligonucleotides targeted to human HER-2 were tested for their effect on the expression of EGFR (HER-1), another member of the epidermal growth factor (EGF) family. It is believed that expression of other human growth factor receptors may also be modulated by HER-2. These growth factor receptors include insulin-like growth factor receptor (IGFR), HER-3, HER-4, platelet-derived growth factor receptor (PDGFR) an fibroblast growth factor receptor (FGFR). The result of this experiment are shown in Table 7. The upper of the two EGFR bands (larger transcript) was measured.

TABLE 7

Effect of antisense oligonucleotides targeted to human HER-2 on human EGFR mRNA expression

| ISIS NO. | SEQ ID: | POSITION ON HER-2 TARGET[2] | TARGET REGION | % INHIB. (AVERAGED; n = number of expts) | |
|---|---|---|---|---|---|
| 9002 | 2 | 1419–1438 | Coding | 26 | n = 3 |
| 9003 | 3 | 3329–3348 | Coding | 5 | n = 2 |
| 9005 | 4 | 4043–4062 | 3'-UTR | 18 | n = 3 |
| 12137 | 7 | scramble of 9003 | | 0 | n = 2 |
| 12882 | 3 | 3329–3348 | Coding | 62 | n = 2 |
| 12883 | 3 | 3329–3348 | Coding | 47 | n = 3 |
| 12884 | 3 | 3329–3348 | Coding | 90 | n = 3 |
| 17391 | 4 | 4043–4062 | 3'-UTR | 29 | n = 1 |
| 17426 | 9 | scramble of 9003 | | 31 | n = 1 |
| 17427 | 10 | scramble of 9002 | | 41 | n = 1 |

It was noted that oligonucleotides targeted to human HER-2 were also able to reduce expression of EGFR.

In order to determine whether this was a nonspecific inhibition or a true pharmacological inhibition, Northern blot assays were done at long (24 hr) vs short (4 hr) time points after treatment of SKOV3 cells with antisense oligonucleotides targeted to HER-2. The results are shown in Table 8.

TABLE 8

Time course of effect of antisense oligonucleotides targeted to human HER-2 on human EGFR and HER-2 mRNA expression

| ISIS NO. | SEQ ID: | POSITION ON HER-2 TARGET[2] | TARGET REGION | % INHIBITION[3] | | | |
|---|---|---|---|---|---|---|---|
| | | | | HER-2 | | EGFR | |
| | | | | 4 hr | 24 hr | 4 hr | 24 hr |
| 9002 | 2 | 1419–1438 | Coding | 76 | 83 | 30 | 29 |
| 9005 | 4 | 4043–4062 | 3'-UTR | 63 | 87 | 3 | 16 |
| 12883 | 3 | 3329–3348 | Coding | 59 | 94 | 5 | 66 |
| 12884 | 3 | 3329–3348 | Coding | 88 | 91 | 25 | 89 |
| 17391 | 4 | 4043–4062 | 3'-UTR | 48 | 65 | 14 | 0 |
| 17397 | 9 | scramble of 9003 | | 6 | 12 | 0 | 0 |
| 17426 | 9 | scramble of 9003 | | 14 | 0 | 3 | 7 |
| 17427 | 10 | scramble of 9002 | | 0 | 0 | 18 | 32 |

[3]n = 1 for all ISIS NOs., except 12883 and 12884 where n = 2

This experiment showed that while oligonucleotides targeted to HER-2 inhibited both EGFR and HER-2 expression at 24 hours, and HER-2 expression was inhibited at the 4 hour time point, EGFR expression was not significantly inhibited at 4 hours, demonstrating that the inhibition of EGFR at later times was not a nonspecific effect. These results indicate that in SKOV3 cells, HER-2 signalling may regulate expression of EGFR.

What is claimed is:

1. An oligonucleotide 12 to 25 nucleotides in length having a nucleotide sequence which comprises at least a portion of SEQ ID NO:2, 3, 4 or 5, wherein said oligonucleotide decreases the expression of human HER-2.

2. The oligonucleotide of claim 1 which contains at least one phosphorothioate intersugar linkage.

3. The oligonucleotide of claim 1 which has at least one 2'-fluoro, 2'-O-alkyl or 2'-O-methoxyethyl modification.

4. The oligonucleotide of claim 1 in which at least one cytosine residue is a 5-methyl cytosine.

5. A method of inhibiting the expression of human HER-2 in cells or tissues comprising contacting said cells or tissues with the oligonucleotide of claim 1.

6. A composition comprising an oligonucleotide 12 to 25 nucleotides in length having a nucleotide sequence which comprises at least a portion of SEQ ID NO: 2, 3, 4 or 5, which is targeted to human HER-2 nucleic acid, wherein said oligonucleotide decreases the expression of human HER-2.

7. A method of inhibiting the expression of human HER-2 in cells or tissues comprising contacting said cells or tissues with the pharmaceutical composition of claim 6.

8. A method of reducing hyperproliferation of human cells comprising contacting proliferating human cells with the composition of claim 6.

9. A method of inhibiting the expression of a human epidermal growth factor receptor in cells or tissues comprising contacting said cells or tissues with an antisense oligonucleotide 12 to 25 nucleotides in length having a nucleotide sequence which comprises at least a portion of SEQ ID NO: 2, 3, 4 or 5, targeted to a nucleic acid encoding human HER-2, so that expression of the human epidermal growth factor receptor is inhibited.

* * * * *

UNITED STATES PATENT AND TRADEMARK OFFICE
CERTIFICATE OF CORRECTION

PATENT NO. : 5,968,748
DATED : October 19, 1999
INVENTOR(S) : Bennett et al.

It is certified that error appears in the above-identified patent and that said Letters Patent is hereby corrected as shown below:

Column 2,
Line 29, please delete "transfecting" and insert therefor -- transfection --.

Column 4,
Line 19, please delete "5=" and insert therefor -- 5' --.

Column 8,
Line 11, please delete "Let" and insert therefor -- et --.
Line 13, please delete "et" and insert therefor -- Let. --.
Line 30, please delete "1" and insert therefor -- al --.

Column 9,
Line 14, please delete "$H_2 CH_2 OCH_3$" and insert therefor -- $CH_2 CH_2 OCH_3$ --.

Column 10,
Line 39, please delete "reservatives" and insert therefor -- preservatives --.

Column 14,
Line 29, please delete " 2.38" and insert therefor -- 24.38 --.

Column 18,
Line 42, please delete "crambled" and insert therefor -- scrambled --.

UNITED STATES PATENT AND TRADEMARK OFFICE
CERTIFICATE OF CORRECTION

PATENT NO. : 5,968,748
DATED : October 19, 1999
INVENTOR(S) : Bennett et al.

It is certified that error appears in the above-identified patent and that said Letters Patent is hereby corrected as shown below:

Item [56] References Cited OTHER PUBLICATIONS
Please delete "Chang et al., "The tumor suppression activity of E1A in HER-s/neu-overexpression breast cancer", *Oncogene*, 1977, 14, 561-568."
and insert therefor -- Chang et al., "The tumor suppression activity of E1A in HER-2/neu-overexpressing breast cancer", *Oncogene*, 1997, 14, 561-568 --.

Wiechen et al., please delete "$P185^{c-34bB-2}$" and insert therefor -- $P185^{C-erbB-2}$ --.

Signed and Sealed this

Fourth Day of December, 2001

Attest:

NICHOLAS P. GODICI
*Attesting Officer*   Acting Director of the United States Patent and Trademark Office